United States Patent [19]

Zenitz

[11] 4,080,380

[45] Mar. 21, 1978

[54] 2-NAPHTHYL-LOWER-ALKYLAMINES

[75] Inventor: Bernard L. Zenitz, Colonie, N.Y.

[73] Assignee: Sterling Drug Inc., New York, N.Y.

[21] Appl. No.: 649,796

[22] Filed: Jan. 16, 1976

Related U.S. Application Data

[63] Continuation-in-part of Ser. No. 542,546, Jan. 20, 1975, Pat. No. 4,005,093.

[51] Int. Cl.² .............................................. C07C 91/28
[52] U.S. Cl. .............................. 260/570.5 P; 260/442; 260/501.11; 260/501.18; 260/501.19; 260/559 R; 260/544 N; 424/316; 424/330
[58] Field of Search .................... 260/570.5 P, 555 S, 260/501.18, 501.19

[56] References Cited

U.S. PATENT DOCUMENTS

| 3,532,749 | 10/1970 | Biel et al. ................. 260/570.5 X |
| 3,573,304 | 3/1971 | Eberle et al. ............... 260/570.5 X |

OTHER PUBLICATIONS

Work, "Chemical Abstracts," vol. 36, pp. 6540-6541 (1942).
Wojahn et al., "Chemical Abstracts," vol. 37, pp. 1996-1997 (1943).

*Primary Examiner*—Robert V. Hines
*Attorney, Agent, or Firm*—William G. Webb; B. Woodrow Wyatt

[57] ABSTRACT

2-Naphthyl-lower-alkylamines, useful as anti-inflammatory agents, are prepared by reaction of a 2-naphthyl-lower-alkanoyl halide with an amine and reduction of the resulting 2-naphthyl-lower-alkanoylamine with a reagent effective to reduce an amide to an amine.

3 Claims, No Drawings

2-NAPHTHYL-LOWER-ALKYLAMINES

RELATED APPLICATIONS

This is a continuation-in-part of my prior, copending application Ser. No. 542,546, filed Jan. 20, 1975, now U.S. Pat. No. 4,005,093, patented Jan. 25, 1977.

BACKGROUND OF THE INVENTION (a) Field of the Invention

This invention relates to 2-naphthyl-lower-alkylamines useful as anti-inflammatory agents.

(b) Description of the Prior Art

A very large class of organic compounds of widely diverse structural types are known to be useful as anti-inflammatory agents, but many of such anti-inflammatory agents are acidic, for example α-(6-methoxy-2-naphthyl)propionic acid known generically as naproxen [Harrison et. al., J. Med. Chem. 13, 203 (1970)]. Such acidic agents are often irritating, and in some cases are ulcerogenic, to the gastric mucosa when administered orally. There is thus a great need for anti-inflammatory agents, for example compounds having a basic amine function, which might be expected to be non-irritating to the gastric mucosa. Although the chemical literature describes numerous types of amine-substituted compounds asserted to have anti-inflammatory activity [see for example U.S. Pat. Nos. 3,770,748, patented Nov. 6, 1973 and 3,803,127, patented Apr. 9, 1974 (N-phenyl-polymethyleneimines); U.S. Pat. Nos. 3,772,311, patented Nov. 13, 1973 and 3,773,772, patented Nov. 20, 1973 (polymethyleneiminolower-alkanoylpyrazoles); U.S. Pat. No. 3,773,944, patented Nov. 20, 1973 (1-[3-aminopropyl]phthalans); U.S. Pat. No. 3,801,594, patented Apr. 2, 1974 (3-amino-lower-alkylindoles); and U.S. Pat. No. 3,810,985, patented May 14, 1974 (4-anilino-1,3,5-triazines)], no such basic compounds are presently known to be commercially available, and none are presently known to be under advanced investigation by pharmacologists for possible commercial development. The search for an effective, non-acidic anti-inflammatory agent for commercial development therefore continues.

SUMMARY OF THE INVENTION

In one of its composition of matter aspects, the invention relates to certain 2-naphthyl-lower-alkylamines:

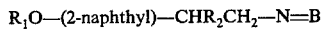

which are useful as anti-inflammatory agents.

In a second composition of matter aspect, the invention relates to certain 2-naphthyl-lower-alkanoylamines:

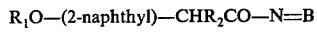

which are useful as intermediates for the preparation of the final products.

DETAILED DESCRIPTION INCLUSIVE OF THE PREFERRED EMBODIMENTS

More specifically, the invention relates to 2-naphthyl-lower-alkylamines, which are useful as anti-inflammatory agents, having the formula:

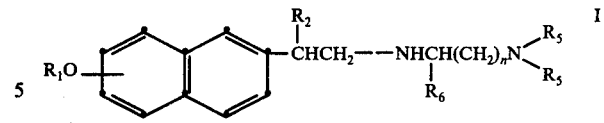

where $R_1$ and $R_2$ each represent hydrogen or lower-alkyl; $R_5$ represents lower-alkyl; $R_6$ represents hydrogen or lower-alkyl; and $n$ represents one of the integers 1, 2 and 3.

Particularly preferred compounds within the ambit of the invention as described above are those having the formula I where $R_1$, $R_2$ and $R_6$ each represent lower-alkyl; and $n$ represents the integer 3.

As used herein, the term lower-alkyl means saturated, monovalent, aliphatic radicals, including branched-chain radicals, of from one to four carbon atoms, for example methyl, ethyl, propyl, isopropyl, butyl, sec.-butyl and isobutyl.

The compounds of formula I are prepared by reaction of an appropriate 2-naphthyl-lower-alkanoyl halide of formula III (prepared by reaction of the corresponding acid of formula II with a thionyl halide) with an appropriate amine of the formula:

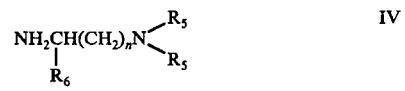

and reduction of the resulting 2-naphthyl-lower-alkanoylamine of formula V with an alkali metal aluminum hydride. The method is represented by the following reaction sequence:

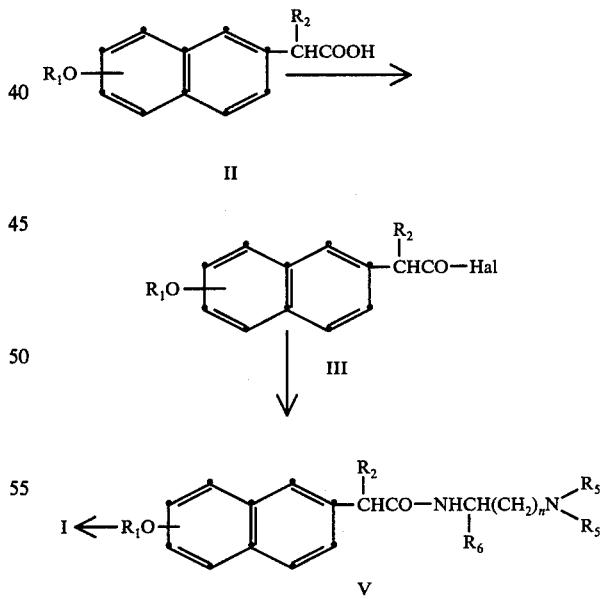

where $R_1$, $R_2$, $R_5$, $R_6$ and $n$ have the meanings given above, and Hal represents halogen.

The preparation of the amides of formula V is essentially a "one-pot" reaction involving reaction of the acid of formula II with a thionyl halide in a non-protolytic organic solvent, for example benzene, toluene or xylene, at the reflux temperature thereof and addition of the acid halide, without isolation or further purification, either in the same solvent or in a different non-protolytic solvent, for example diethyl ether, dioxane or tetrahydrofuran, to a solution of the amine of formula IV in a non-protolytic organic solvent. The latter reaction is preferably carried out at ambient temperature and in the presence either of a molar excess of the amine or in the presence of an acid-acceptor, for example pyridine, a tri-lower-alkylamine, dimethylaniline or an alkali metal carbonate.

The amines of formula IV are known compounds as are the 2-naphthyl-lower-alkanoic acids of formula II. (See for example Fried, U.S. Pat. No. 3,626,012, patented Dec. 7, 1971).

The novel compounds of the instant invention are the compounds of formula I and the acid-addition salts thereof. The compounds of formula I in free base form are converted to the acid-addition salt form by interaction of the base with an acid. In like manner, the free base can be regenerated from the acid-addition salt form in the conventional manner, that is by treating the salts with cold, weak aqueous bases, for example alkali metal carbonates and alkali metal bicarbonates. The bases thus regenerated can then be interacted with the same or a different acid to give back the same or a different acid-addition salt. Thus the novel bases and all of their acid-addition salts are readily interconvertible.

It will thus be appreciated that formula I not only represents the structural configuration of the bases of formula I but is also representative of the structural entity which is common to all of the compounds of formula I, whether in the form of the free base or in the form of the acid-addition salts of the base. It has been found that by virtue of this common structural entity, the bases and their acid-addition salts have inherent pharmacological activity of a type to be more fully described hereinbelow. This inherent pharmacological activity can be enjoyed in useful form for pharmaceutical purposes by employing the free bases themselves or the acid-addition salts formed from pharmaceutically-acceptable acids, that is, acids whose anions are innocuous to the animal organism in effective doses of the salts so that beneficial properties inherent in the common structural entity represented by the free bases is not vitiated by side effects ascribable to the anions.

In utilizing this pharmacological activity of the salts of the invention, it is preferred, of course, to use pharmaceutically-acceptable salts. Although water-insolubility, high toxicity, or lack of crystalline character may make some particular salt species unsuitable or less desirable for use as such in a given pharmaceutical application, the water-insoluble or toxic salts can be converted to the corresponding pharmaceutically-acceptable bases by decomposition of the salt with aqueous base as explained above, or alternatively, they can be converted to any desired pharmaceutically-acceptable acid-addition salt by double decomposition reactions involving the anion, for example by ion-exchange procedures.

Moreover, apart from their usefulness in pharmaceutical applications, the salts are useful as characterizing or identifying derivatives of the free bases or in isolation or purification procedures. Like all of the acid-addition salts, such characterizing or purification salt derivatives can, if desired, be used to regenerate the pharmaceutically-acceptable free bases by reaction of the salts with aqueous base, or alternatively can be converted to a pharmaceutically-acceptable acid-addition salt by, for example, ion-exchange procedures.

It will be appreciated from the foregoing that all of the acid-addition salts of the new bases are useful and valuable compounds, regardless of considerations of solubility, toxicity, physical form, and the like, and are accordingly within the purview of the instant invention.

The novel feature of the compounds of the invention, then, resides in the concept of the bases and cationic forms of the new 2-naphthyl-lower-alkylamines and not in any particular acid moiety or acid anion associated with the salt forms of the compounds; rather, the acid moieties or anions which can be associated in the salt forms are in themselves neither novel nor critical and therefore can be any acid anion or acid-like substance capable of salt formation with the bases. In fact, in aqueous solutions, the base form or water-soluble acid-addition salt form of the compounds of the invention both possess a common protonated cation or ammonium ion.

Thus appropriate acid-addition salts are those derived from such diverse acids as formic acid, acetic acid, isobutyric acid, alpha-mercaptopropionic acid, malic acid, fumaric acid, succinic acid, succinamic acid, tartaric acid, citric acid, lactic acid, benzoic acid, 4-methoxybenzoic acid, phthalic acid, anthranilic acid, 1-naphthalenecarboxylic acid, cinnamic acid, cyclohexanecarboxylic acid, mandelic acid, tropic acid, crotonic acid, acetylenedicarboxylic acid, sorbic acid, 2-furancarboxylic acid, cholic acid, pyrenecarboxylic acid, 2-pyridinecarboxylic acid, 3-indoleacetic acid, quinic acid, sulfamic acid, methanesulfonic acid, isethionic acid, benzenesulfonic acid, p-toluenesulfonic acid, benzenesulfinic acid, butylarsonic acid, diethylphosphonic acid, p-aminophenylarsinic acid, phenylstibnic acid, phenylphosphinous acid, methylphosphinic acid, phenylphosphinic acid, hydrofluoric acid, hydrochloric acid, hydrobromic acid, hydriodic acid, perchloric acid, nitric acid, sulfuric acid, phosphoric acid, hydrocyanic acid, phosphotungstic acid, molybdic acid, phosphomolybdic acid, pyrophosphoric acid, arsenic acid, picric acid, picrolonic acid, barbituric acid, boron trifluoride, and the like.

The acid-addition salts are prepared by reacting the free base and acid in an organic solvent and isolating the salt directly or by concentration of the solution.

Due to the presence of at least one and as many as two asymmetric centers in the compounds of the invention (i.e. the carbon atoms to which the $R_2$ and $R_6$ groups when lower-alkyl are attached), the compounds of the invention can exist in stereochemically isomeric forms, which are all considered to be within the purview of the invention. If desired, the isolation or the production of a particular stereochemical form can be accomplished by application of general principles known in the art.

In standard pharmacological test procedures, the compounds of formula I have been found to possess anti-inflammatory activity and are useful as anti-inflammatory agents. Anti-inflammatory activity was determined using (1) the inhibition of carrageenin-induced foot edema test essentially described by Van Arman et al., J. Pharmacol. Exptl. Therap. 150, 328 (1965) as modified by Winter et al., Proc. Soc. Exp. Biol. and Med. 111, 544 (1962) and (2) a modification of the inhibition of adjuvant-induced arthritis test described by Pierson, J. Chronic Diseases 16, 863 (1963) and Glenn et al., Am. J. Vet. Res. 26, 1180 (1965).

The compounds of the invention can be prepared for use by incorporating them in unit dosage form as tablets or capsules for oral administration either alone or in combination with suitable adjuvants such as calcium carbonate, starch, lactose, talc, magnesium stearate, gum acacia, and the like. Still further, the compounds can be formulated for oral administration in aqueous alcohol, glycol or oil solutions or oil-water emulsions in the same manner as conventional medicinal substances are prepared.

The molecular structures of the compounds of the invention were assigned on the basis of study of their infrared, ultraviolet and NMR spectra, and confirmed by the correspondence between calculated and found values for elementary analyses for the elements.

The following examples will further illustrate the invention without, however, limiting it thereto. All melting points are uncorrected.

EXAMPLE 1

A solution of 30.6 g. (0.13 mole) of d,l-α-(6-methoxy-2-naphthyl)propionic acid and 15.8 ml. (26.4 g., 0.22 mole) of thionyl chloride in 47 ml. of benzene was refluxed for three and one half hours and then taken to dryness in vacuo. There was thus obtained 34.8 g. of crude d,l-α-(6-methoxy-2-naphthyl)propionyl chloride as an oil, 16.5 g. (0.061 mole) of which was dissolved in 29 ml. of diethyl ether and added dropwise with stirring to a solution of 9.7 g. (0.067 mole) of N', N'-diethyl-1,4-pentanediamine and 7.4 g. (0.073 mole) of triethylamine in 29 ml. of anhydrous diethyl ether while cooling with an external ice bath. The mixture was stirred at ambient temperature for three days, diluted with additional ether and filtered. The solid filter was extracted once with hot ether and then washed with 10% sodium hydroxide and extracted twice with benzene. The benzene extracts, on drying over anhydrous sodium sulfate and evaporation to dryness, gave 13.1 g. of N-[α-(6-methoxy-2-naphthyl)propionyl]-N-[5-(N',N'-diethylamino)-2-pentyl]amine.

The latter (0.032 mole), dissolved in 50 ml. of anhydrous diethyl ether, was added in small portions to a suspension of 2.43 g. (0.064 mole) of lithium aluminum hydride in 50 ml. of diethyl ether while maintaining the temperature between 15° and 20° C. by cooling with a water bath. When addition was complete, the reaction was stirred for about 12 hours at ambient temperature and then treated over a ten minute period with 2.4 ml. of water and 2.4 ml. of 50% sodium hydroxide and stirred at ambient temperature for about 10 minutes. The mixture was filtered through filter aid and the insoluble filter washed with diethyl ether. The combined organic solution was washed with saturated brine solution, dried over anhydrous sodium sulfate and evaporated to dryness to give 10.3 g. of crude product which was chromatographed on alumina and eluted with a solution of diethyl ether:hexane:isopropylamine (20:75:5). There was thus obtained 4.0 g. of N-[2-(6-methoxy-2-naphthyl)-2-methylethyl]-N-[5-(N',N'-diethylamino)-2-pentyl]amine as a pale yellow oil.

The latter, tested in the rat using the carrageenin edema test at 0.08 and 0.324 millimole/kg. (p.o.) gave, respectively, 28% and 26% inhibition of inflammation, and when tested in the adjuvant arthritis test at 0.16 millimole/kg. (p.o.) gave 73% inhibition.

EXAMPLES 2–7

Following a procedure similar to that described above in Example 1, the following compounds of formula I are prepared:

EXAMPLE 2

N-[2-(6-Methoxy-2-naphthyl)-2-methylethyl]-N-[2-(N',N'-diethylamino)ethyl]amine, prepared by reaction of d,l-α-(6-methoxy-2-naphthyl)propionyl chloride with N,N-diethylethylenediamine and reduction of the resulting N-[α-(6-methoxy-2-naphthyl)propionyl]N-[2-(N',N'-diethylamino)ethyl]amine;

EXAMPLE 3

N-[2-(6-Methoxy-2-naphthyl)-2-methylethyl]-N-[5-(N',N'-dimethylamino)-2-pentyl]amine, prepared by reaction of d,l-α-(6-methoxy-2-naphthyl)propionyl chloride with 5-dimethylamino-2-pentylamine and reduction of the resulting N-[α-(6-methoxy-2-naphthyl)-propionyl]-N-[5-(N',N'-dimethylamino)-2-pentyl]amine with lithium aluminum hydride;

EXAMPLE 4

N-[2-(6-Methoxy-2-naphthyl)-2-methylethyl]-N-[3-(N',N'-dipropylamino)-1-propyl]amine, prepared by reaction of d,l-α-(6-methoxy-2-naphthyl)propionyl chloride with N,N-dipropyl-1,3-propanediamine and reduction of the resulting N-[α-(6-methoxy-2-naphthyl)propionyl]-N-[3-(N',N'-dipropylamino)-1-propyl]amine with lithium aluminum hydride;

EXAMPLE 5

N-[2-(6-Methoxy-2-naphthyl)-2-methylethyl]-N-[3-(N',N'-diisopropylamino)-1-propyl]amine, prepared by reaction of d,l-α-(6-methoxy-2-naphthyl)propionyl chloride with N,N-diisopropyl-1,3-propanediamine and reduction of the resulting N-[α-(6-methoxy-2-naphthyl)propionyl]-N-[3-(N',N'-diisopropylamino)-1-propyl]amine with lithium aluminum hydride;

EXAMPLE 6

N-[2-(6-Methoxy-2-naphthyl)-2-methylethyl]-N-[7-(N',N'-diethylamino)-4-heptyl]amine, prepared by reaction of d,l-α-(6-methoxy-2-naphthyl)propionyl chloride with 7-diethylamino-4-heptylamine and reduction of the resulting N-[α-(6-methoxy-2-naphthyl)propionyl]-N-[7-(N',N'-diethylamino)-4-heptyl]amine with lithium aluminum hydride; and

EXAMPLE 7

N-[2-(6-Methoxy-2-naphthyl)-2-methylethyl]-N-[3-(diisobutylamino)-1-propyl]amine, prepared by reaction of d,l-α-(6-methoxy-2-naphthyl)propionyl chloride with N,N-diisobutyl-1,3-propanediamine and reduction of the resulting N-[α-(6-methoxy-2-naphthyl)propionyl]-N-[3-(diisobutylamino)-1-propyl]amine with lithium aluminum hydride.

I claim:

1. A compound having the formula:

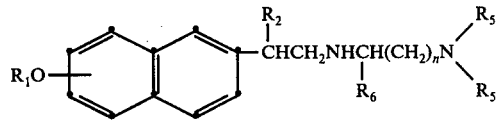

where $R_1$ and $R_2$ each represent hydrogen or lower-alkyl; $R_5$ represents lower-alkyl; $R_6$ represents hydrogen or lower-alkyl; and $n$ represents one of the integers 1, 2 and 3.

2. A compound according to claim 1 where $R_1$, $R_2$ and $R_6$ each represent lower-alkyl; and $n$ represents the integer 3.

3. N-[2-(6-Methoxy-2-naphthyl)-2-methylethyl]-N-[5-(N',N'-dimethylamino)-2-pentyl]amine according to claim 2.

* * * * *